United States Patent
Czapski

(10) Patent No.: US 12,122,327 B2
(45) Date of Patent: Oct. 22, 2024

(54) MOUNTING AND STABILIZING BRACKET FOR THE CAR GRILLE

(71) Applicant: Krzysztof Czapski, Piaseczno (PL)

(72) Inventor: Krzysztof Czapski, Piaseczno (PL)

( * ) Notice: Subject to any disclaimer, the term of this patent is extended or adjusted under 35 U.S.C. 154(b) by 142 days.

(21) Appl. No.: 18/000,342

(22) PCT Filed: Jun. 7, 2021

(86) PCT No.: PCT/PL2021/050039
§ 371 (c)(1),
(2) Date: Nov. 30, 2022

(87) PCT Pub. No.: WO2021/251841
PCT Pub. Date: Dec. 16, 2021

(65) Prior Publication Data
US 2023/0211735 A1 Jul. 6, 2023

(30) Foreign Application Priority Data

Jun. 8, 2020 (PL) .......................................... 434246

(51) Int. Cl.
*B60R 11/00* (2006.01)
*B60R 7/08* (2006.01)

(52) U.S. Cl.
CPC ......... *B60R 7/08* (2013.01); *B60R 2011/0008* (2013.01)

(58) Field of Classification Search
CPC ..... B60R 2011/0008; B60R 2011/0059; B60R 2011/008; B60R 2011/0005

USPC .......................................................... 224/483
See application file for complete search history.

(56) References Cited

U.S. PATENT DOCUMENTS

| | | | |
|---|---|---|---|
| 6,698,071 B1 * | 3/2004 | Greer, Jr. ................. | F16B 2/10 24/522 |
| 10,493,177 B2 * | 12/2019 | Knapp .................... | A61L 9/012 |
| 2012/0067970 A1 * | 3/2012 | Hossein ............... | B60H 3/0028 239/34 |
| 2013/0064721 A1 | 3/2013 | Chabot | |
| 2015/0203052 A1 * | 7/2015 | Wolfsen ................. | B60R 11/00 432/5 |
| 2018/0193511 A1 | 7/2018 | Knapp et al. | |

FOREIGN PATENT DOCUMENTS

CN 207360037 U 5/2018
DE 202012010226 U1 2/2013

* cited by examiner

*Primary Examiner* — Adam J Waggenspack
(74) *Attorney, Agent, or Firm* — Cherskov Flaynik & Gurda, LLC

(57) ABSTRACT

A bracket mounted on a car ventilation grille, in particular for fragrance carriers, consisting of a frame and fastening and stabilizing elements, characterized in that the frame is a U-shaped semi-closed structure provided with two arms, and the fastening and stabilizing elements are at least two sliding flexible fastening pads with a thickness less than or equal to the distance between the frame arms, at least one of which is applied to the first frame arm and at least one of which is applied to the second frame arm.

3 Claims, 3 Drawing Sheets

MOUNTING AND STABILIZING BRACKET FOR THE CAR GRILLE

RELATED APPLICATIONS

This application is a national phase entry of PCT international phase patent application No. PCT/PL2021/050039, filed Jun. 7, 2021, which claims the benefit of priority of Polish Patent Application No. P.434246, filed Jun. 8, 2020. The entire contents of the above-referenced applications and of all priority documents referenced in the Application Data Sheet filed herewith are hereby incorporated by reference for all purposes.

The subject of the invention is a bracket for the car grille.

Due to their location in relation to the driver, car vents are an attractive place to attach various add-ons such as ornaments, phone holders, and fragrance carriers. An obstacle to taking advantage of this attractive location is the variety of designs of said grilles between different car models.

The purpose of the invention was to provide a new car grille mount, the design of which would enable universal use.

The essence of the invention is a bracket mounted on the car ventilation grille, in particular for fragrance carriers, consisting of a frame and fastening and stabilizing elements, characterized in that the frame is a U-shaped semi-closed structure provided with two arms, and the fastening and stabilizing elements are at least two sliding flexible fastening pads with a thickness less than or equal to the distance between the frame arms, at least one of which is applied to the first frame arm and at least one of which is applied to the second frame arm.

Preferably, the thickness of the mounting pads is less than or equal to half the distance between the arms of the frame.

Preferably, the fastening and stabilizing elements of the bracket are four sliding flexible fastening pads arranged in pairs on the frame arms.

The invention provides the following advantages:
versatility of the solution makes it possible to apply it to any type of grille in any car;
low production cost;
ease of installation;
reliability of operation;
dampens/reduces vibrations transmitted from the grille to the fragrance carrier;

The subject-matter of the invention is depicted in the examples shown in the drawing wherein FIG. 1 schematically presents the bracket according to the invention;

EXAMPLE 1

Car grille bracket according to the invention, shown in FIG. 1-4, is designed specifically for mounting an air freshener or fragrance carrier.

Figure 1:
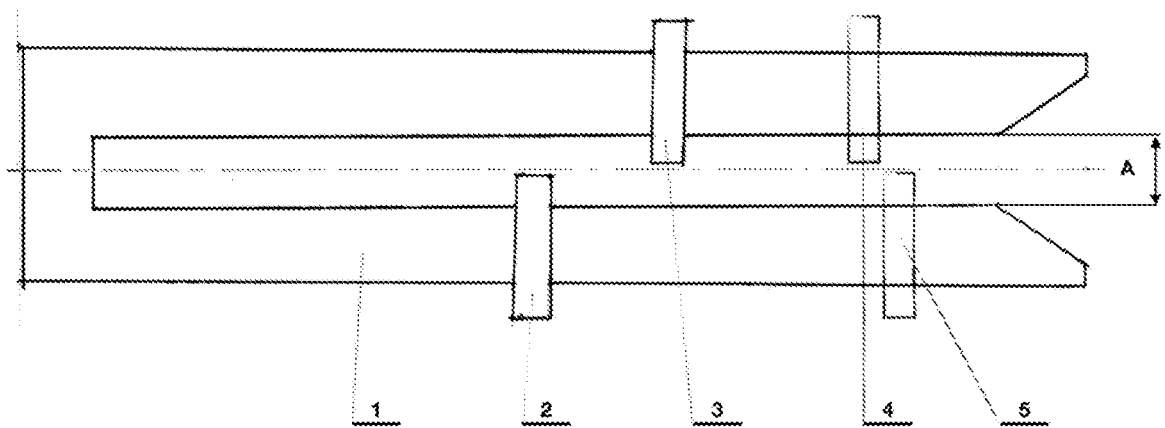

As shown in FIG. 1, the bracket according to the invention consists of the frame 1 provided with fastening and stabilizing elements, which is a U-shaped semi-closed structure provided with two arms. In this embodiment, the frame is wooden, while other materials can be used to make it, e.g. plastic, metal, minerals, glass and other materials of natural origin.

Figure 2:
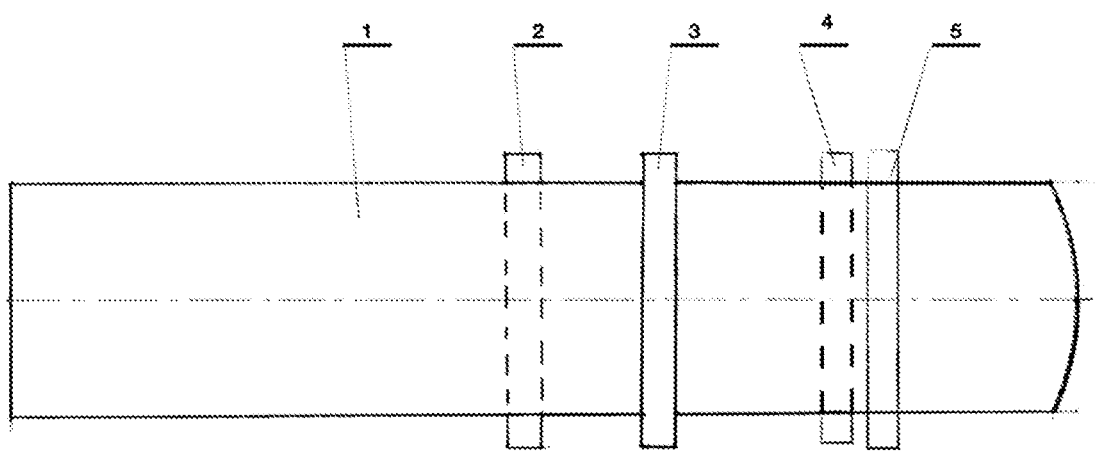
FIG. 2 shows a view of a single bracket frame arm according to the invention.

Whereas said fastening and stabilizing elements are sliding flexible fastening pads 2, 3, 4 and 5 applied to the frame arms 1, wherein the pads 2 and 5 are applied to the first frame arm 1 and the pads 3 and 4 are applied to the second frame arm 1 (FIG. 2).

In this non-limiting embodiment, the pads 2, 3, 4 and 5 are in the form of rubber rings, while other materials (e.g. silicone or plastic) can be used to make them. Due to the flexibility of the pads 2 and 3, the frame 1 of the bracket minimises the transmission of vibrations to the edge of the grille on which the bracket is fixed.

The addition of pads 4 and 5 reinforces the bracket stabilizing effect by allowing the frame 1 of the bracket to be fixed and stabilized even on a sheet of paper. The mounting and stabilizing effect of the frame is achieved by moving and placing the individual mounting pads into the optimal position.

Figure 3:
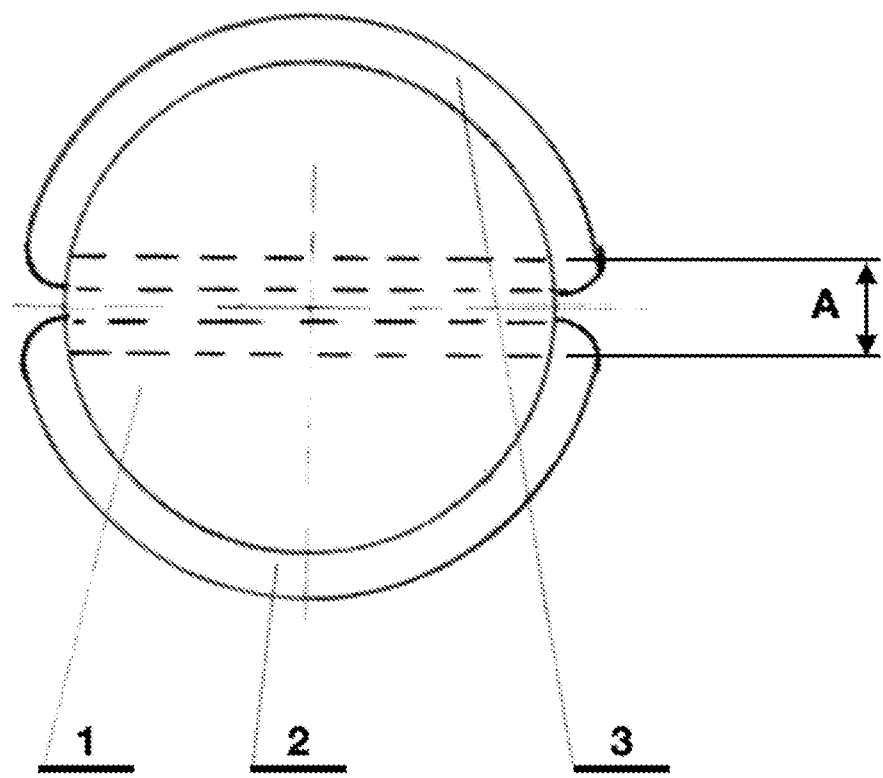
FIG. 3 shows a cross-sectional view of the bracket according to the invention, detailing the thickness of the basic pads.
Figure 4:
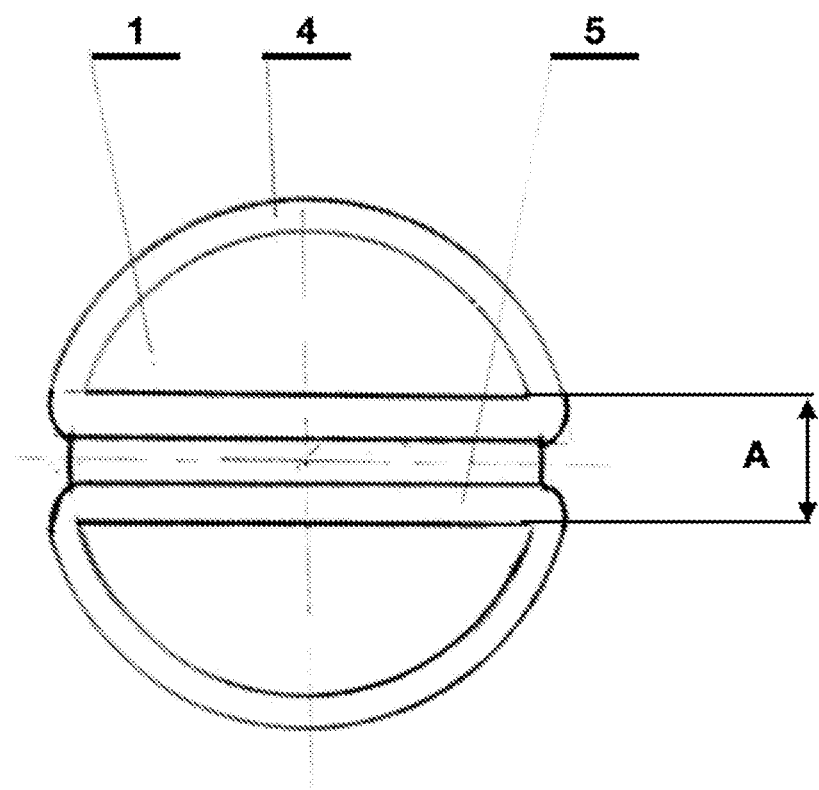
FIG. 4 shows a cross-sectional view of the bracket according to the invention detailing the thickness of the complementary pads.

In this non-limiting embodiment, the thickness of the mounting pads 2, 3, 4 and 5 applied to the arms of the frame 1 of the bracket is ½ A, i.e. half the distance between the arms of the frame 1. Whereas the maximum thickness of mounting pads 2, 3, 4 and 5 placed on the arms of the frame 1 of the bracket cannot exceed the value equal to A—i.e. the distance between the arms of the frame 1 (FIGS. 3 and 4).

EXAMPLE 2

The bracket as in embodiment 1, except that the thickness of the mounting pads 2, 3, 4 and 5 applied to the frame arms 1 of the bracket is equal to A.

EXAMPLE 3

The bracket as in embodiment 1, except that the thickness of the mounting pads 2, 3, 4 and 5 applied to the frame arms 1 of the bracket is ¼ A.

EXAMPLE 4

The bracket as in embodiment 1, except that the pads 2, 3, 4 and 5 are in the form of silicone rings and have a thickness of ¾ A.

The invention claimed is:

1. A bracket configured to be mounted on a car ventilation grille, comprising a frame and fastening and stabilizing elements, characterized in that the frame is a U-shaped semi-closed structure provided with two arms, and the fastening and stabilizing elements are at least two sliding flexible fastening pads with a thickness less than or equal to the distance between the frame arms, at least one of which is applied to the first frame arm and at least one of which is applied to the second frame arm.

2. The bracket according to claim 1, characterized in that the thickness of the mounting pads is less than or equal to half the distance between the arms of the frame.

3. The bracket according to claim 1, characterized in that the fastening and stabilizing elements are four sliding flexible fastening pads arranged in pairs on the frame arms.

\* \* \* \* \*